United States Patent [19]

Fischer

[11] Patent Number: 5,425,641
[45] Date of Patent: Jun. 20, 1995

[54] DENTAL KIT AND PROCESS FOR SEALING PITS AND FISSURES IN ENAMEL

[75] Inventor: Dan E. Fischer, Sandy, Utah

[73] Assignee: Ultradent Products, Inc., Jordan, Utah

[21] Appl. No.: 97,873

[22] Filed: Jul. 27, 1993

[51] Int. Cl.⁶ .............................................. A61C 5/04
[52] U.S. Cl. .................................. 433/226; 433/228.1
[58] Field of Search ............. 433/215, 216, 226, 228.1

[56] References Cited

U.S. PATENT DOCUMENTS

| | | | |
|---|---|---|---|
| 4,514,527 | 4/1985 | Bowen | 433/228.1 X |
| 4,521,550 | 6/1985 | Bowen | 523/116 |
| 4,535,102 | 8/1985 | Kusumoto et al. | 433/228.1 X |
| 4,588,756 | 5/1986 | Bowen | 433/228.1 X |
| 4,659,751 | 4/1987 | Bowen | 433/228.1 X |
| 4,872,936 | 10/1989 | Engelbrecht | 433/228.1 X |
| 4,964,911 | 10/1990 | Ibsen et al. | 433/228.1 X |
| 5,270,351 | 12/1993 | Bowen | 433/228.1 X |

Primary Examiner—Nicholas D. Lucchesi
Attorney, Agent, or Firm—Workman Nydegger Seeley

[57] ABSTRACT

Dental compositions used in sealing pits and fissures in tooth enamel to aid in the prevention of dental caries are disclosed, along with methods for their use. The enamel is cleaned and prepared using conventional methods, etched with either aqueous phosphoric acid or citric acid, treated with a drying/priming agent containing either anhydrous ethyl alcohol or anhydrous acetone and the adduct of N(p-tolyl)glycine and glycidyl methacrylate ("NTG-GMA"), and sealed with a resinous sealing material which includes 2,2-bis(hydroxyphenyl)propane diglycidylmethacrylate.

The sealing material may also include other additives such as filler materials, thinning agents, hydrophilic resins, and photoinitiators. The compositions may be adapted to be applied by means of a syringe delivery system.

55 Claims, No Drawings

DENTAL KIT AND PROCESS FOR SEALING PITS AND FISSURES IN ENAMEL

BACKGROUND OF THE INVENTION

1. The Field of the Invention

This invention relates to improved dental kits and procedures for sealing noncarious or slightly carious pits and fissures in teeth to aid in the prevention of dental caries. More specifically, the invention relates to an improved dental pit and fissure sealant kit consisting of an etching material, a drying/priming agent, and a resinous sealant which is applied over naturally occurring noncarious dental pits and fissures or after carious lesion removal to protect a tooth from cariogenic attack.

2. The Relevant Technology

With the appearance of resins and resinous composites in the field of dentistry, a variety of uses and bonding techniques have been developed besides the mere filling of cavities. In some cases, composites, the name for highly filled resins, can take the place of traditional silver-mercury amalgam, particularly when the hardness and durability of amalgam is not required. In addition, lesser filled resins are ideal for many cosmetic alterations of the teeth, such as applying a layer of white resinous material for concealing unattractive stains, or otherwise brightening one's smile.

Unfilled and low filled resins have been found to be useful in filling noncarious pits and fissures found naturally in teeth, usually molars. While often not the product of tooth decay but natural tooth development and formation, such pits and fissures are usually more difficult to clean and are ideal locations for cariogenic agents to lodge, eventually resulting in the formation of caries (or cavities).

The depth and width of naturally occurring pits and fissures varies greatly among the population. Generally, the deeper the fissure, the greater the chance the tooth will eventually suffer decay. As a measure to prevent tooth decay and cavity formation, dentists have more recently begun to partially fill the deepest portions of these pits and fissures with resinous materials.

Before placing an appropriate resinous material within the pit or fissure being treated, the enamel is normally prepared in order to allow reliable adhesion of the polymeric resin material to the enamel. By methods known in the art, the enamel is physically scraped or buffed with a rotary burr in order to remove all foreign materials such as dental plaque or tartar.

The enamel is then chemically etched with an aqueous acid such as phosphoric or citric acid to further prepare the tooth surface to be bonded. Etching selectively removes various components of the enamel, thereby creating microscopic irregularities and undercuts. The surface is then dried with air and the pits and fissures are sealed with the resinous filling material.

However, air drying alone is not capable of completely drying the enamel and the area within the pits and fissures. Because teeth and enamel are located in a 100% humid environment, a thin film of water can adhere to the enamel with tenacity. Sources of moisture include the saliva present in the patient's mouth, the aqueous acid etch, and even ambient water vapor present in the mouth. Due to the small width, combined with the relatively large depth, of typical pits and fissures, it is especially difficult for air drying alone to effectively remove moisture from within the pits and fissures. In addition, most compressed dental air sources unfortunately contain moisture.

The failure to completely dry the enamel surface prior to applying the pit and fissure sealant decreases the ability of the sealant to adequately bond to the enamel, which increases the likelihood of subsequent microleakage of the bonded filling. Hence, the success of the sealing process often correlates to the success of completely drying the enamel surface.

Resinous materials tend to shrink upon curing causing them to pull away from the tooth surface, especially if a strong bond has not been achieved between the resin and the enamel surface. Such bonding is more difficult if the enamel has not been adequately dried of excess moisture.

When there is microleakage of moisture into the interface between the enamel surface and the sealant, the anticarious properties of the sealant are greatly diminished. In fact, microleakage probably increases the possibility of developing caries in the pit or fissure that was treated because of the difficulty of removing a cariogenic agent (bacteria or their byproducts) that has crept into the interface between the tooth and sealant.

Ordinary cleaning regimens such as brushing or gargling are inadequate in cleaning, flushing out or otherwise removing cariogenic agents that might creep into the interface between the sealant and enamel. Thus, microleakage tends to undermine the reason for sealing the pit or fissure in the first place.

Improvements in the bond between resin and enamel have been achieved through the use of drying agents, usually water miscible organic solvents such as acetone or ethyl alcohol. While using such solvents has the advantage over simply drying the enamel by air, they still do not result in completely reliable bonding between resin and enamel. This is mainly due to the enormous difference in the relative polarities between enamel and most resins, enamel being extremely hydrophilic, while resins are largely hydrophobic. Thus, resins and enamel have a natural tendency to repel each other.

Thus, even if the excess water has been removed from the tooth, the problem remains that the largely hydrophobic resins found in pit and fissure sealants cannot effectively "wet" or make sufficiently intimate, interactive contact with the very hydrophilic enamel surface. This is yet another impediment of prior art sealing methods in attaining reliable adhesion between the resinous sealant and tooth enamel.

In view of the foregoing, it would be an advancement in the dental art to provide dental compositions and procedures for applying resinous sealants to dental pits and fissures which would result in a more reliable adhesion of the sealant and the elimination of microleakage. It will be appreciated that it would also be a significant improvement over the prior art to provide dental compositions and procedures which would substantially eliminate the separation of the applied sealant from the enamel surface due to the inability to effectively remove the thin film of water from the tooth surface. Therefore, what is needed are compounds and procedures for more effectively removing water from tooth enamel surfaces prior to the application of resinous sealing materials.

It would be a further advancement in the dental art to provide compositions and procedures which effectively "wet" the enamel surface and reduce the hydrophilic nature of the surface so that the hydrophobic sealing material can make more intimate contact with the enamel. Such compositions and procedures would result in greater bond strengths between the enamel and sealing material and significantly reduce or eliminate the microleakage caused by shrinkage of the polymerizing composite materials in conjunction with the lack of adequate initial wetting of the enamel surface by the applied resinous sealing composite.

Such compositions and procedures for achieving these results are set forth and claimed herein.

SUMMARY AND OBJECTS OF THE PRESENT INVENTION

The present invention embraces dental compositions and methods which result in extremely reliable bonds between an applied pit and fissure sealing material (comprised of an unfilled or low-filled resin) and the tooth enamel surface. Such a sure bond is effective in substantially reducing the incidence of subsequent microleakage of the sealant after the sealant has set. By eliminating (or at least substantially reducing) microleakage, the compositions and methods of the present invention are far more effective in sealing pits and fissures—the prevention of tooth decay by providing a protective layer of nondecayable resins over the areas where the enamel is most susceptible to decay and where cariogenic agents can most easily lodge and build up.

More particularly, the present invention relates to dental compositions which together constitute a dental kit including an etching solution, a drying/priming agent, and a resinous sealing material. The present invention also relates to methods for using the dental kit. The drying/priming agent is able to simultaneously dry the tooth surface of any residual moisture, while being able to "prewet" or prime the tooth surface with a bipolar substance. This prewetting of the enamel surface greatly reduces the hydrophilic nature of the enamel surface, thereby allowing the resinous sealing materials to make more intimate initial contact with the enamel surface during the application of the resinous sealant.

In a preferred method of applying the compositions of the present invention, the enamel surface to be treated is first cleaned by conventional cleaning or polishing methods known in the art. One method that works well is using a rotary bur in conjunction with cleaning abrasives known in the art.

After the surface has been cleared of foreign material, the enamel surface is etched using an etching solution comprising a moderately weak aqueous acid solution, such as aqueous phosphoric acid. In addition to phosphoric acid, the etching solution may comprise other acids such as citric acid, maleic acid, or dilute nitric acid. The acid etching of the tooth enamel surface selectively strips away part of the mineral surface, thereby creating microscopic irregularities and undercuts. This leaves the enamel with a superior bonding surface to which a resinous sealing material can ultimately bond. After applying the etching solution, the enamel is usually rinsed with water.

A drying/priming agent is next applied, followed by brief aspiration to remove any remaining drying/priming agent from the pit or fissure of the enamel being treated. The drying/priming agent comprises a solution of any volatile, water miscible organic solvent, such as ethanol or acetone (but preferably ethanol), and the adduct of N(p-tolyl)glycine and glycidyl methacrylate, or N-(2-hydroxy-3-((2-methyl-1-oxo-2-propenyl)oxy)-propyl)-N-tolyl glycine, (commonly known, and hereinafter referred to, as "NTG-GMA"). It is often preferable to use the sodium salt of NTG-GMA due to its lower cost. However, studies have shown that the magnesium salt of NTG-GMA is even more preferred than the sodium salt. Only half as much of the magnesium salt of NTG-GMA produces equivalent or even superior results compared to the sodium salts of NTG-GMA.

The water miscible organic solvent mixes with and removes the residual water remaining on the enamel surface. It is believed that due to the ability of NTG-GMA to wet the enamel surface and its significantly high affinity for water, the combination of NTG-GMA and solvent is able to remove most or all of the remaining water molecules that may yet adhere to the highly hygroscopic enamel surface, particularly enamel that has been cleaned and etched.

Even more important is the ability of the NTG-GMA to "prewet" or prime the enamel surface in preparation for the subsequent application of the hydrophobic resin. Because NTG-GMA has both hydrophilic and hydrophobic moieties, it is able to make intimate, wetting contact with the enamel surface. The hydrophilic ends come into contact with the enamel surface, while the hydrophobic ends orient themselves away from the enamel surface. This wetting creates a thin film of NTG-GMA on the surface of the enamel which is largely hydrophobic due to the favorable positioning of the hydrophobic moieties of NTG-GMA, which are repelled away from the enamel surface. Without this prewetting, the relatively hydrophobic resinous sealing material would have a more difficult time making intimate bonding contact with the very hydrophilic micro irregularities and undercuts of the etched enamel surface, as is the case with most commercial preparations available on the market.

In the present application, tests have shown that the concentration of NTG-GMA within the drying/priming agent is preferably within the range from between about 0.1% to about 3% by weight. As the concentration increases beyond this range, the incidence of microleakage has been shown to increase significantly. More preferred concentrations of NTG-GMA are within the range from between about 0.4% to about 1.5% by weight, while the most preferred concentrations are within the range from between about 0.7% to about 1.2%.

Finally, an appropriate resinous sealing material is then applied to the pit or fissure being treated. The sealing material preferably includes a relatively high viscosity resin such as Bis-GMA (the common name for 2,2bis(hydroxyphenyl)propane diglycidylmethacrylate). The resinous sealing material may also contain inorganic fillers (such as fluoro-alumina silicate), photoinitiators (such as camphor quinone), and thinning agents (such as TEG-DMA, the common name for triethyleneglycol dimenthacrylate). Other copolymerizable resins such as urethane dimethacrylate (hereinafter "UDM") can also be included.

While the compositions disclosed herein can be applied using conventional application methods, they are especially useful in conjunction with syringe delivery methods. With the aid of a syringe, the compositions of the present invention can be conveniently and effectively applied. Indeed, it is this ease of application that increases the efficiency, duplicability, and, hence, the consistency and reliability of the compositions of the present invention.

From the foregoing, it will be appreciated that an object of the present invention is the development of dental compositions and methods for effectively sealing pits and fissures in tooth enamel surfaces to help prevent dental caries.

Another object and feature of the present invention is the development of dental compositions and methods for more effectively establishing reliable bonds between the applied sealants and enamel surfaces to reduce the incidence of subsequent microleakage of the sealant, which can occur whenever there is inadequate bonding of the sealant to the enamel surface.

Yet another object of the present invention is the development of superior drying/priming agents and methods as part of the comprehensive dental kits disclosed herein which more effectively remove the water which tends to remain on the enamel surface using conventional drying agents or methods prior to the application of the resinous sealing materials.

A further object of the present invention is the development of superior drying/priming agents and methods as part of the comprehensive dental kits disclosed herein which effectively "prewet" or prime the enamel surface, allowing the largely hydrophobic resinous sealing materials to make more intimate bonding contact with the enamel surface.

These and other objects and features of the present invention will become more fully apparent from the following description and appended claims, or may be learned by the practice of the invention.

DETAILED DESCRIPTION OF THE PREFERRED EMBODIMENTS

The present invention relates to compositions and methods for sealing pits and fissures in tooth enamel. A dental kit incorporating the present invention includes an etching solution to prepare the surface of the enamel, a drying/priming agent, and a resinous sealant material. The result is a protective coating over the pit or fissure in the treated enamel that protects the tooth from potential decay. The compositions and methods according to the present invention are effective in substantially reducing or even eliminating the incidence of microleakage.

Microleakage can occur whenever there is an inadequate bond between the resinous sealant and the enamel. This allows cavity-causing agents, such as bacteria and their byproducts, to seep into the space between the sealant material and enamel, thus wholly undermining the purpose for sealing the enamel in the first place.

Before applying the compositions of the present invention, it is usually preferable to preliminarily remove any foreign material from the enamel surface being treated (such as plaque, tartar, pellicle, etc.) and to "freshen" the enamel surface by scraping, buffing, or polishing the enamel surface by conventional teeth cleaning means. It is common to roughen the enamel and fissure walls with a rotary bur.

The first step of the present invention involves etching the enamel tooth surface with a moderately strong aqueous acid. A typical etching solution includes aqueous phosphoric acid having a concentration (measured in units of weight to volume) that is preferably within the range from between about 10% to about 60%, more preferably within the range from between about 20% to about 50%, and most preferably within the range from between about 30% to about 45%. An example of an etching solution which includes phosphoric acid is Ultra-Etch®, which is available from Ultradent Products, Inc., of South Jordan, Utah.

The acid etching solution etches the enamel surface by selectively stripping away a small amount of the calcified mineral surface, which results in the creation of microscopic irregularities and undercuts. This creates an irregular bonding surface to which a resinous sealing material can more reliably adhere.

Although phosphoric acid has been found to work well in etching the enamel tooth surface, other acids having similar properties are also within the scope of the present invention, including citric acid, maleic acid, or dilute nitric acid. Phosphoric acid is presently preferred because it has low toxicity and has a proven history of being effective.

After the enamel surface has been etched, a drying/priming agent is applied to remove any water remaining on the enamel surface, and to prime the surface so that the subsequently applied sealant can better adhere to the etched surface. The drying/priming agent preferably comprises a solution of ethyl alcohol and NTG-GMA, with the concentration of NTG-GMA preferably being within the range from between about 0.1% to about 3% by weight of the drying agent, more preferably between about 0.4% to about 1.5%, and most preferably between about 0.7% to about 1.2.%. It is preferable to use the sodium salt of NTG-GMA because of its lower cost, without sacrificing any effectiveness, and even more preferable to use the magnesium salt of NTG-GMA. NTG-GMA and its magnesium and sodium salts are available from Esschem Co. of Essington, Pa. Primadry™ is an example of a currently preferred embodiment of the drying/priming agent containing NTG-GMA and ethyl alcohol within the scope of the present invention, and can be obtained from Ultradent Products, Inc.

Alternatively, the ethyl alcohol in the above solutions can be replaced with acetone, which appears to work equally well in drying enamel surfaces. Nevertheless, ethyl alcohol is the more preferred organic solvent of choice, particularly for syringe delivery.

A number of patents disclose the use of NTG-GMA in order to help prepare the bonding surfaces of certain dental tissues. These include U.S. Pat. Nos. 4,514,527; 4,521,550; 4,588,756; and 4,659,751 to Bowen and U.S. Pat. No. 4,964,911 to Ibsen et al. However, in each of these references, it is recommended that NTG-GMA be used in concentrations of 10% or more. To the extent that NTG-GMA was used in such high concentrations, such a reference would not be relevant to nor would in any way anticipate the particular use of NTG-GMA in the present invention. In some of these references NTG-GMA was also used in combination with other monomers so that the NTG-GMA would specifically polymerize and become part of the resinous polymer.

Application of the drying/priming agent containing NTG-GMA achieves two separate but related goals, each of which facilitates more intimate and reliable bonding of the sealant material to the enamel surface. First, the ethyl alcohol (or, alternatively, acetone) in the drying/priming solution mixes with and flushes out any excess water persisting within the tooth pits and fissures. Each of these solvents forms volatile azeotropic mixtures with water which are much more volatile than water itself.

Removal of these azeotropic mixtures is further facilitated by air drying of the tooth surface. At the same time, it is believed that the NTG-GMA wets the enamel surface thus breaking up the surface tension and helping to remove any water which might remain on the enamel surface even after flushing it with solvent. Thus, most of the thin film of water which tends to otherwise persist on the hygroscopic enamel surface is supplanted by the NTG-GMA.

Second, because NTG-GMA is apparently able to "wet" the enamel surface it greatly reduces the hydrophilic nature of the enamel, thus allowing more intimate initial contact of the subsequently applied hydrophobic resinous sealing material. This simultaneous wetting and reduction of the enamel surface tension occurs because NTG-GMA contains both hydrophilic and hydrophobic moieties. It is believed that the hydrophilic moieties interact with the enamel surface, while the more hydrophobic ends are oriented away from the enamel surface. Because the hydrophobic ends are oriented away from the enamel surface, the effect is that the enamel is coated with a microthin layer of what effectively is a hydrophobic substance with which the largely hydrophobic resinous sealing materials such as Bis-GMA can more easily interact.

This prewetting or priming of the enamel surface by the NTG-GMA allows the resinous sealing materials to make more close, intimate initial contact with the enamel surface when applied. The result is a much more reliable bond between resin and enamel than has been heretofore possible using prior art methods. Experiments have shown that treating the enamel with a drying/priming agent which includes NTG-GMA (in the concentrations set forth herein) prior to applying a resinous sealing material yields a much stronger and more durable bond between the sealing material and enamel than possible with any of the prior art bonding methods. They also indicate that enamel treated according to the present invention exhibits substantially lower microleakage than with prior art compositions and methods.

Although relatively good bonds between the enamel and sealing material can be obtained by using 3M Drying Agent (which comprises acetone), superior bonding is only possible when NTG-GMA is included in the stated preferred amounts.

As discussed below, a preferred resinous sealing material includes a resin such as Bis-GMA, along with appropriate thinning agents, fillers, hydrophilic resins, and photoinitiators that are known in the art. The sealing material preferably includes Bis-GMA in a concentration within the range from between about 20% to about 80% by weight, more preferably within the range from between about 30% to about 20%, and most preferably within the range from between about 35% to about 65%. An example of a resinous sealing material containing Bis-GMA as the primary resinous constituent is UltraSeal®XT ™, which is available from Ultradent Products, Inc.

A preferred inorganic filler material that can be added to the Bis-GMA containing sealing material is fluoro-ilumina silicate. A preferred photoinitiator is camphor quinone, which is preferably included in an amount ranging from about 0.1% to about 0.6% by weight of the sealing material. A preferred thinning agent is TEG-DMA. A copolymerizable hydrophilic resin that can be added to the sealing material is UDM.

As the resinous sealing material sets up or cures, it undergoes a series of polymerization and cross-linking reactions. The NTG-GMA is reactively compatible with resinous monomers such as Bis-GMA and appears to be readily incorporated into the final polymerized and cross-linked resinous matrix of the sealant.

As stated above, one of the advantages of the compositions of the present invention is that they are especially compatible with syringe delivery systems. Thus, they can be conveniently and effectively applied. Moreover, it is precisely this ease of application which increases the efficiency and duplicability of the application, resulting in greater consistency and reliability of the seals obtained through using the compositions of the present invention.

The reduction of microleakage of pit and fissure sealants according to the compositions and methods stated herein has been demonstrated by a series of experimental tests.

Experimental Test 1

A number of test teeth were etched with a 40% solution of phosphoric acid. After that, some of the teeth were dried and primed with a drying/priming agent comprising ethyl alcohol and NTG-GMA in varying concentrations within the range from 0% to about 10%. Others were simply allowed to air dry. Finally the teeth were sealed with a resinous sealant that included Bis-GMA.

After the sealant was allowed to set for 48 hours an aqueous silver nitrate solution was applied to the treated enamel surfaces and allowed sufficient time in which to seep into any existing microfissures between the sealant and the enamel and to stain the enamel surface. The surfaces of the test teeth were then ground in a direction perpendicular to the bond between the sealant and the tooth surface.

By observing the depth of the silver nitrate stain, the extent of microleakage in the interface between the sealant and the enamel was measured for each tooth. The extent of microleakage is significant because it inversely correlates to the strength of the bond; that is, it decreases as the bond between the sealant and enamel increases.

It was found that there was a significant reduction in microleakage in the enamel seals that were applied according to the present invention as opposed to those that were applied after (1) simple air aspiration of the tooth surface, (2) drying of the surface with ethyl alcohol only (0% NTG-GMA), or (3) drying of the tooth surface with drying/priming agents having a concentration of substantially more than about 3% NTG-GMA.

This preliminary test indicated that drying/priming agents that contained at least some NTG-GMA, even in the smallest quantities, work better than those that do not. In addition, the test indicated that drying/priming agents that contain too much NTG-GMA (more than 5%) do not work as well as those containing less.

Experimental Test 2

In a second experiment, dental kits containing one of three drying agents comprising ethyl alcohol and either 1%, 4% or 5% NTG-GMA, respectively, were tested for microleakage. The sealant in each case included Bis-GMA resin. Fifteen test molars of unknown history, which had been stored in 0.05% thymol solution, were used in this test.

Preliminarily, each of the teeth was rinsed for 30 seconds, treated with a rubber cap prophylaxis using a pumice/water mixture, and rinsed again for 20 seconds. After this initial cleaning step, the teeth were randomly divided into three groups containing five teeth each. Each of the teeth was subsequently etched for 30 seconds with an aqueous 40% phosphoric acid solution and then rinsed with an air-water spray for about 30 seconds.

Each of the teeth was then treated with one of the three drying/priming agents for five seconds, followed by gentle air drying. Group 1 was treated with a drying/priming agent which contained 1% NTG-GMA; Group 2 was treated with a drying/priming agent which contained 4% NTG-GMA; and Group 3 was treated with a drying/priming agent which contained 5% NTG-GMA.

Finally, each of the test teeth was filled with a pit and fissure sealant containing UDM and light cured for 60 seconds. The sealed teeth were then stored in tap water for 24 hours prior to their being analyzed.

During the analysis, each of the tooth samples was first thermocycled for 4000 cycles in water from 5° C. to 55° C. ±2° C., with a dwell time of 45 seconds in each bath, with a transfer time of 3 seconds. After the tooth samples were thermocycled, the apices of the roots were sealed with sticky wax that extended approximately 2 mm up the root surface. Two coats of nail varnish were applied to within 1 mm of the margin of the sealant. The samples were then stored in 0.5% basic fuchsin dye solution for 24 hours.

Following storage in the dye solution, the tooth samples were cleaned by first scraping them with a laboratory knife, and then by polishing them with a slurry of flour of pumice and water to remove the nail varnish and sticky wax. Each of the tooth samples was then cut into four sections approximately 1 mm in thickness using an Isomet ® low-speed saw using water coolant. The sections were immediately placed on a glass microscope slide and stabilized with sticky wax.

Each sample was evaluated for dye penetration using magnification of 20X. Microleakage was scored according to the presence or absence of dye penetration of any amount. In other words, if any dye penetration was noted at any place on any section of the sample, it was scored as leakage.

Of the five tooth samples of Group 1, which were treated with the drying/priming agent containing 1% NTG-GMA, none of the samples exhibited any leakage whatsoever. Of the five tooth samples of Group 2, which were treated with the drying/priming agent containing 4% NTG-GMA, one sample in five (or 20% of the samples) had leakage. Finally, of the five tooth samples of Group 3, which were treated with the drying/priming agent containing 5% NTG-GMA, two samples in five (or 40% of the samples) had leakage. This test clearly indicated that the best results were obtained when using a drying/priming agent that contains 1% NTG-GMA rather than 4% or 5% NTG-GMA, respectively.

Experimental Test 3

Test 2 was repeated in every respect except that there was no air drying after applying the drying/priming agent. Each of the samples showed some degree of microleakage. Thus, it can be concluded that air drying following the application of the drying/priming agent is an important procedure.

Experimental Test 4

From the results of Experimental Tests 2 and 3, it was clear that the best results were obtained when a drying/priming agent containing about 1% NTG-GMA was used, followed by air drying, as compared to using a drying/priming agents containing either 4% or 5% NTG-GMA. With this in mind, a quantitative test was carried out using two different drying/priming agents, one containing 1% NTG-GMA and the other containing 2% NTG-GMA in order to determine the optimum concentration of NTG-GMA. Aside from using drying/priming agents with different concentrations of NTG-GMA, the teeth were prepared in the same manner as those in Experimental Test 2.

Twenty-six teeth were divided into two groups of thirteen. The teeth within Group 1 were treated with the drying/priming agent containing 1% NTG-GMA, while those in Group 2 were treated with the drying/priming agent containing 2% NTG-GMA. The results of Experimental Test 5 are set for in Table 1 as follows, with the amount of penetration being measured in millimeters:

TABLE 1

|  | Group 1 | Group 2 |
| --- | --- | --- |
|  | 0.000 | 0.091 |
|  | 0.000 | 0.019 |
|  | 0.000 | 0.069 |
|  | 0.003 | 0.079 |
|  | 0.000 | 0.099 |
|  | 0.000 | 0.000 |
|  | 0.023 | 0.000 |
|  | 0.000 | 0.000 |
|  | 0.000 | 0.013 |
|  | 0.000 | 0.048 |
|  | 0.000 | 0.194 |
|  | 0.006 | 0.178 |
|  | 0.000 | 0.169 |
| Mean Leakage: | 0.002 | 0.067 |
| Std. Dev. | 0.006 | 0.067 |

Experimental Test 5

From the results of Experimental Tests 2, 3 and 4, it appeared that the best results can be obtained by using a drying/priming agent that contains about 1% NTG-GMA, followed by air drying, as compared to using a drying/priming agent containing 2% NTG-GMA. With this in mind, a second quantitative test was carried out using two other drying/priming agents besides the one having 1% NTG-GMA, the first containing 0.4% NTG-GMA and the other containing 1.5% NTG-GMA, in order to determine the optimum concentration of NTG-GMA. Except for altering the drying/priming agents to have different concentrations of NTG-GMA, the teeth in this experimental test were otherwise prepared in the same manner as those in Experimental Test 2.

Thirty test teeth were divided into three groups of ten teeth each. The teeth within Groups 1-3 were treated with drying/priming agents comprising ethyl alcohol and NTG-GMA having concentrations of 0.4%, 1%, and 1.5%, respectively. The results of Experimental Test 5 are set forth in Table 2 as follows, with the amount of penetration being measured in millimeters:

TABLE 2

| Group 1 | Group 2 | Group 3 |
| --- | --- | --- |
| 0.013 | 0.015 | 0.295 |

TABLE 2-continued

|  | Group 1 | Group 2 | Group 3 |
|---|---|---|---|
|  | 0.002 | 0.000 | 0.059 |
|  | 0.038 | 0.039 | 0.065 |
|  | 0.018 | 0.025 | 0.019 |
|  | 0.199 | 0.020 | 0.145 |
|  | 0.228 | 0.031 | 0.075 |
|  | 0.110 | 0.000 | 0.037 |
|  | 0.217 | 0.000 | 0.112 |
|  | 0.107 | 0.062 | 0.050 |
|  | 0.000 | 0.065 | 0.049 |
| Mean: | 0.093 | 0.026 | 0.091 |
| Std. Dev.: | 0.093 | 0.024 | 0.081 |
| Range: | 0.000–0.228 | 0.000–0.065 | 0.019–0.295 |

Statistical analysis was carried out by one-way ANOVA. This test confirmed that microleakage can be minimized by using a drying/priming agent which contains about 1% NTG-GMA. Although it is possible that the optimum concentration of NTG-GMA may be something other than 1%, it appears that it is somewhere between 0.4% and 1.5%.

EXAMPLES OF THE PREFERRED EMBODIMENTS

As set forth above, various tests have been performed comparing the amount of microleakage resulting from the use of different compositions and methods for sealing pits and fissures of tooth enamel. Below are specific examples of the compositions and methods which have been created according to the present invention.

Example 1

A dental kit including compositions for sealing pits and fissures in tooth enamel was created which had the following components which are designed to be applied in successive steps:
 1. an etching solution containing aqueous phosphoric acid (40% weight to volume);
 2. a drying/priming agent comprising: ethyl alcohol; and NTG-GMA (1% by weight); and
 3. a resinous sealant comprising Bis-GMA (22.6% by weight).

This dental kit was used to seal the enamel of ten different teeth according to the method set forth in Experimental Test 5. The total time which elapsed during the application of the pit and fissure sealing kit compositions, including time for etching, drying, priming, and sealing each tooth, was approximately 2½ minutes. This is excluding the one minute it took to rinse and clean the teeth preparatory to applying the compositions herein.

The resulting bond between the enamel and sealant material was excellent and there was little or no detectable microleakage.

Example 2

A dental kit including compositions for sealing pits and fissures in tooth enamel was created having the following components which are designed to be applied in successive steps:
 1. an etching solution containing aqueous phosphoric acid (40% weight to volume);
 2. a drying/priming agent comprising: ethyl alcohol; and NTG-GMA (0.4% by weight); and
 3. a resinous sealant comprising Bis-GMA (22.6% by weight).

This dental kit was used to seal the enamel of ten different teeth according to the method set forth in Experimental Test 5. Accordingly, the total time which elapsed during the application of the pit and fissure sealing kit compositions, including time for etching, drying, priming, and sealing each tooth, was approximately 2½ minutes. This is excluding the one minute it took rinse and clean the teeth preparatory to applying the compositions herein.

The resulting bond between the enamel and sealant material was excellent and there was only minimally detectable microleakage.

Example 3

A dental kit including compositions for sealing pits and fissures in tooth enamel was created having the following components which are designed to be applied in successive steps:
 1. an etching solution containing aqueous phosphoric acid (40% weight to volume);
 2. a drying/priming agent comprising: ethyl alcohol; and NTG-GMA (1.5% by weight); and
 3. a resinous sealant comprising Bis-GMA (22.6% by weight).

This dental kit was used to seal the enamel of ten different teeth according to the method set forth in Experimental Test 5. Accordingly, the total time which elapsed during the application of the pit and fissure sealing kit compositions, including time for etching, drying, priming, and sealing each tooth, was approximately 2½ minutes. This is excluding the one minute it took rinse and clean the teeth preparatory to applying the compositions herein.

The resulting bond between the enamel and sealant material was excellent and there was only a minimal amount of detectable microleakage.

Example 4

A dental kit including compositions for sealing pits and fissures in tooth-enamel was created having the following components, which are designed to be applied in successive steps:
 1. an etching solution containing aqueous phosphoric acid (40% weight to volume);
 2. a drying/priming agent comprising: ethyl alcohol; and NTG-GMA (2% by weight); and
 3. a resinous sealant comprising Bis-GMA (22.6% by weight).

This dental kit was used to seal the enamel of thirteen different teeth according to the method set forth in Experimental Test 4. Accordingly, the total time which elapsed during the application of the pit and fissure sealing kit compositions, including time for etching, drying, priming, and sealing each tooth, was approximately 2½ minutes. This is excluding the one minute it took to rinse and clean the teeth preparatory to applying the compositions herein.

The resulting bond between the enamel and sealant material was excellent and there was zero or only minimal detectable microleakage.

Example 5

A dental kit including compositions for sealing pits and fissures in tooth enamel was created having the following components which are designed to be applied in successive steps:
 1. an etching solution containing aqueous phosphoric acid (40% weight to volume);
 2. a drying/priming agent comprising: ethyl alcohol; and NTG-GMA (4% by weight); and 3. a resinous sealant comprising Bis-GMA (22.6% by weight).

This dental kit was used to seal the enamel of five different teeth according to the method set forth in Experimental Test 2. Accordingly, the total time which elapsed during the application of the pit and fissure sealing kit compositions, including time for etching, drying, priming, and sealing each tooth, was approximately 2½ minutes. This is excluding the one minute it took to rinse and clean the teeth preparatory to applying the compositions herein.

The resulting bond between the enamel and sealant material was excellent, although a visual, qualitative test showed detectable microleakage in one of the five tooth samples. Nevertheless, four of the five samples exhibited no visual microleakage under a magnification of 20X.

Example 6

A dental kit including compositions for sealing pits and fissures in tooth enamel was created having the following components which are designed to be applied in successive steps:
1. an etching solution containing aqueous phosphoric acid (40% weight to volume);
2. a drying/priming agent comprising: ethyl alcohol; and NTG-GMA (5% by weight); and
3. a resinous sealant comprising Bis-GMA (22.6% by weight).

This dental kit was used to seal the enamel of five different teeth according to the method set forth in Experimental Test 2. Accordingly, the total time which elapsed during the application of the pit and fissure sealing kit compositions, including time for etching, drying, priming, and sealing each teeth, was approximately 2½ minutes. This is excluding the one minute it took to rinse and clean the teeth preparatory to applying the compositions herein.

The resulting bond between the enamel and sealant material was excellent, although a visual, qualitative test showed detectable microleakage in two of the five tooth samples. Nevertheless, four of the five samples exhibited no visual microleakage under a magnification of 20X.

Examples 1-6 demonstrate that superior bonds between sealant and enamel can be obtained by using a drying/priming agent that comprises ethyl alcohol and NTG-GMA in concentrations ranging from between about 0.4% to about 4%. When a drying/priming agent having NTG-GMA in a concentration of 5% was used, the amount of microleakage increased dramatically. It further appears that optimum results are obtained by using a drying/priming agent in which the concentration of NTG-GMA is about 1%.

While the examples which follow are hypothetical in nature, they are based upon similar mix designs which have either been made, or which were calculated and extrapolated from actual mixes. However, these examples are presented this way in order to more specifically teach those skilled in the art the compositions and methods of the present invention.

Examples 7-17

The compositions for sealing pits and fissures set forth in the following examples are identical to those of Examples 1-6 except that varying amounts of NTG-GMA are used in the drying/priming agent composition and the enamel etching solution is altered to comprise aqueous phosphoric acid in a concentration of 35% weight to volume. In all other respects, the dental kits are the same as in Examples 1-6.

| Example | Amount of NTG-GMA |
|---------|-------------------|
| 7       | 0.5%              |
| 8       | 0.6%              |
| 9       | 0.7%              |
| 10      | 0.8%              |
| 11      | 0.9%              |
| 12      | 1.1%              |
| 13      | 1.2%              |
| 14      | 1.3%              |
| 15      | 1.4%              |

The amount of subsequent microleakage of the sealant applied using the compositions of Examples 7-15 is minimal, with average leakage being no higher than 0.093 mm for each of the formulations, in some cases being around 0.026 and possibly below. The drying/priming agents that contain NTG-GMA in concentrations closer to about 1% result in the smallest degree of subsequent microleakage.

Examples 16-18

The compositions for sealing pits and fissures set forth in the following examples are identical to those of Examples 1-6 except that varying amounts of NTG-GMA are used in the drying/priming agent composition. In all other respects the dental kits are the same.

| Example | Amount of NTG-GMA |
|---------|-------------------|
| 16      | 0.1%              |
| 17      | 0.2%              |
| 18      | 0.3%              |

The amount of subsequent microleakage of the sealant applied using the compositions of Examples 16-18 is minimal, with average leakage being around 0.093 mm for each of the formulations.

Examples 19-25

The compositions for sealing pits and fissures set forth in the following examples are identical to those of Examples 1-6 except that varying amounts of NTG-GMA are used in the drying/priming agent composition. In all other respects the dental kits are the same.

| Example | Amount of NTG-GMA |
|---------|-------------------|
| 19      | 1.6%              |
| 20      | 1.8%              |
| 21      | 2.2%              |
| 22      | 2.4%              |
| 23      | 2.6%              |
| 24      | 2.8%              |
| 25      | 3%                |

The amount of subsequent microleakage of the sealant applied using the compositions of Examples 19-25 is minimal, with average leakage being around 0.091 mm for each of the formulations that contain lesser amounts of NTG-GMA, with the degree of microleakage increasing slightly as the NTG-GMA is increased.

Examples 26-33

The compositions for sealing pits and fissures set forth in the following examples are identical to those of Example 1 except that acid etching solutions containing varying concentrations of aqueous phosphoric acid (expressed as weight to volume) are used.

| Example | Strength of Phosphoric Acid |
|---------|----------------------------|
| 26 | 20% |
| 27 | 25% |
| 28 | 30% |
| 29 | 35% |
| 30 | 45% |
| 31 | 50% |
| 32 | 55% |
| 33 | 60% |

The amount of subsequent microleakage of sealants applied using the compositions of Examples 26–33 is similar to that obtained in Example 1. However, as the strength of the phosphoric acid solution increases, the time it takes to etch the enamel surface decreases slightly, although each of the solutions only etches the enamel until the acid has been neutralized by the reaction with the carbonates within the teeth. Higher concentrations of etching solutions may be expected to result in further etching before neutralization compared to less concentrated solutions.

Examples 34–38

The compositions for sealing pits and fissures of Examples 34–38 are identical to those of Examples 1–5, respectively, except that the drying/priming agent contains acetone instead of ethyl alcohol. The amount of subsequent microleakage of sealant applied using the compositions in each of Examples 34–38 is similar to that of Examples 1–5.

Examples 39–43

The compositions for sealing pits and fissures of Examples 39–43 are identical to those of Examples 1–5, respectively, except that the sealing material in each case further includes UDM as a copolymerizable hydrophilic resin within the sealing material, which thickens the sealing material and aids in syringe delivery. The amount of subsequent microleakage of sealant applied using the compositions of Examples 39–43 are similar to those obtained using the compositions of Examples 1–5.

Examples 44–48

The compositions for sealing pits and fissures of Examples 44–48 are identical to those of Examples 1–5, respectively, except that the sealing material in each case further includes camphor quinone as a photoinitiator in the amount of about 0.3% by weight. The amount of subsequent microleakage of sealant applied using the compositions of Examples 44–48 are similar to those obtained using the compositions of Examples 1–5.

From the foregoing, it will be appreciated that the present invention provides novel compositions and processes for sealing pits and fissures in tooth enamel which result in zero, or only minimal, subsequent microleakage. Thus, the pit and fissure sealant compositions and methods of the present invention aid in the prevention of caries in the pits and fissures where they are most likely to form.

The present invention provides improved compositions and methods for preparing the tooth enamel surface by acid etching, drying/priming agents for removing all or substantially all of the residual moisture and for prewetting or priming the enamel surface with a resin compatible substance, and finally resinous sealing materials for sealing the enamel pit and fissure.

Further, the drying/priming agent of the present invention includes a water miscible organic solvent which is able to remove most of the residual moisture on the enamel surface, while the NTG-GMA is able to prewet the enamel surface and decrease the surface tension of the enamel surface, thereby aiding the removal of any remaining moisture.

Further this prewetting of the highly hydrophilic enamel surface helps the sealing material to make more intimate initial contact with the enamel to which it is applied.

The present invention may be embodied in other specific forms and for other specific uses without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. A dental kit for sealing pits and fissures in tooth enamel as an anticarious procedure comprising:
   (1) an etching solution consisting essentially of an aqueous phosphoric acid solution having a concentration such that it is capable of significantly etching tooth enamel in order to create a more irregular enamel surface to which a polymerizable-resin-containing sealing material can more readily adhere;
   (2) a drying/priming agent comprising:
      (a) a water miscible organic solvent; and
      (b) NTG-GMA having a concentration in a range from about 0.1% to about 3% by weight of the drying/priming agent; and
   (3) a sealing material including a polymerizable resin in a concentration sufficient to bond to etched and substantially dried tooth enamel and to substantially seal the pits and fissures of the tooth enamel.

2. A dental kit for sealing pits and fissures in tooth enamel as defined in claim 1, wherein the aqueous phosphoric acid solution has a concentration in a range from about 10% to about 60% weight to volume.

3. A dental kit for sealing pits and fissures in tooth enamel as defined in claim 1, wherein the aqueous phosphoric acid solution has a concentration in a range from about 20% to about 50% weight to volume.

4. A dental kit for sealing pits and fissures in tooth enamel as defined in claim 1, wherein the aqueous phosphoric acid solution has a concentration in a range from about 30% to about 45% weight to volume.

5. A dental kit for sealing pits and fissures in tooth enamel as defined in claim 1, wherein the aqueous phosphoric acid solution has a concentration of about 35% weight to volume.

6. A dental kit for sealing pits and fissures in tooth enamel as defined in claim 1, wherein the water miscible organic solvent comprises ethyl alcohol.

7. A dental kit for sealing pits and fissures in tooth enamel as defined in claim 1, wherein the water miscible organic solvent comprises anhydrous ethyl alcohol.

8. A dental kit for sealing pits and fissures in tooth enamel as defined in claim 1, wherein the water miscible organic solvent comprises acetone.

9. A dental kit for sealing pits and fissures in tooth enamel as defined in claim 1, wherein the concentration of the NTG-GMA in a drying/priming agent is within the range from about 0.4% to about 1.5% by weight of the drying/priming agent.

10. A dental kit for sealing pits and fissures in tooth enamel as defined in claim 1, wherein the concentration of the NTG-GMA in a drying/priming agent is within the range from about 0.7% to about 1.2% by weight of the drying/priming agent.

11. A dental kit for sealing pits and fissures in tooth enamel as defined in claim 1, wherein the concentration of the NTG-GMA within the drying/priming agent is about 1% by weight of the drying/priming agent.

12. A dental kit for sealing pits and fissures in tooth enamel as defined in claim 1, wherein the polymerizable resin comprises Bis-GMA.

13. A dental kit for sealing pits and fissures in tooth enamel as defined in claim 12, wherein the Bis-GMA has a concentration in a range from about 20% to about 80% by weight of the sealing material.

14. A dental kit for sealing pits and fissures in tooth enamel as defined in claim 12, wherein the Bis-GMA has a concentration in a range from about 30% to about 70% by weight of the sealing material.

15. A dental kit for sealing pits and fissures in tooth enamel as defined in claim 12, wherein the Bis-GMA has a concentration in a range from about 35% to about 65% by weight of the sealing material.

16. A dental kit for sealing pits and fissures in tooth enamel as defined in claim 12, wherein the sealing material comprises a photoinitiator.

17. A dental kit for sealing pits and fissures in tooth enamel as defined in claim 16, wherein the photo-initiator includes camphor quinone.

18. A dental kit for sealing pits and fissures in tooth enamel as defined in claim 17, wherein the camphor quinone is included in an amount of about 0.3% by weight of the sealing material.

19. A dental kit for sealing pits and fissures in tooth enamel as defined in claim 1, wherein the sealing material includes UDM.

20. A dental kit for sealing pits and fissures in tooth enamel as defined in claim 1, wherein the sealing material includes a filler material comprising fluoro-alumina silicate.

21. A dental kit for sealing pits and fissures in tooth enamel as defined in claim 1, wherein the sealing material includes a thinning agent comprising TEG-DMA.

22. A dental kit for sealing pits and fissures in tooth enamel as defined in claim 1, wherein the NTG-GMA comprises the sodium salt of NTG-GMA.

23. A dental kit for sealing pits and fissures in tooth enamel as defined in claim 1, wherein the NTG-GMA comprises the magnesium salt of NTG-GMA.

24. A dental kit for sealing pits and fissures in tooth enamel as an anticarious procedure comprising:
   (1) an etching solution consisting essentially of an aqueous phosphoric acid solution capable of significantly etching tooth enamel in order to create a more irregular enamel surface to which a polymerizable-resin-containing sealing material can more readily adhere, the aqueous phosphoric acid solution having a phosphoric acid concentration in a range from about 10% to about 60% weight to volume;
   (2) a drying/priming agent comprising:
      (a) a water miscible solvent selected from the group consisting of ethyl alcohol and acetone; and
      (b) NTG-GMA having a concentration in a range from about 0.1% to about 3% by weight of the drying/priming agent; and
   (3) a sealing material comprising a polymerizable resin in a concentration sufficient to bond to etched and substantially dried tooth enamel and to substantially seal the tooth enamel, the polymerizable resin including Bis-GMA having a concentration in a range from about 20% to about 80% by weight of the sealing material.

25. A dental kit for sealing pits and fissures in tooth enamel as defined in claim 24, wherein the aqueous phosphoric acid solution has a phosphoric acid concentration in a range from about 20% to about 50% weight to volume.

26. A dental kit for sealing pits and fissures in tooth enamel as defined in clam 24, wherein the aqueous phosphoric acid solution has a phosphoric acid concentration in a range from about 30% to about 45% weight to volume.

27. A dental kit for sealing pits and fissures in tooth enamel as defined in claim 24, wherein the NTG-GMA within the drying/priming agent has a concentration in a range from about 0.7% to about 1.2% by weight of the drying/priming agent.

28. A dental kit for sealing pits and fissures in tooth enamel as defined in claim 24, wherein the NTG-GMA within the drying/priming agent has a concentration of about 1% by weight of the priming/drying agent.

29. A dental kit for sealing pits and fissures in tooth enamel as defined in claim 24, wherein the water miscible organic solvent is selected from the group consisting of ethyl alcohol, anhydrous ethyl alcohol, and acetone.

30. A dental kit for sealing pits and fissures in tooth enamel as defined in claim 24, wherein the sealing material includes UDM.

31. A dental kit for sealing pits and fissures in tooth enamel as defined in claim 24, wherein the sealing material includes TEG-DMA.

32. A dental kit for sealing pits and fissures in tooth enamel as defined in claim 24, wherein the NTG-GMA comprises the sodium salt of NTG-GMA.

33. A dental kit for sealing pits and fissures in tooth enamel as defined in claim 24, wherein the NTG-GMA comprises the magnesium salt of NTG-GMA.

34. A method for sealing pits and fissures in a tooth enamel surface as an anticarious procedure comprising the steps of:
   (1) etching an area of the surface of the tooth enamel to be treated with an etching solution consisting essentially of an aqueous phosphoric acid solution in a concentration such that it is capable of significantly etching tooth enamel in order to creme a more irregular enamel surface to which a polymerizable-resin-containing sealing material can more readily adhere, the etching solution being applied to an area surrounding and including the area of the tooth enamel surface being treated;
   (2) applying a drying/priming agent comprising:
      (a) a water miscible organic solvent; and
      (b) NTG-GMA having a concentration in a range from about 0.1% to about 3% by weight of the drying/priming agent, the drying/priming agent being applied to an area surrounding and including the area of the tooth enamel surface being treated; and (3) sealing the enamel surface with a sealing material comprising a polymerizable resin in a concentration sufficient to bond to and substantially seal the area of the tooth enamel surface being treated.

35. A method for sealing pits and fissures in tooth enamel as defined in claim 34, the method including the step of drying the enamel surface with air after step (2) but before step (3).

36. A method for sealing pits and fissures in tooth enamel as defined in claim 34, the method including the stop of air aspirating the enamel surface after step (2) but before step (3).

37. A method for sealing pits and fissures in tooth enamel as defined in claim 34, wherein the NTG-GMA comprises the sodium salt of NTG-GMA.

38. A method for sealing pits and fissures in tooth enamel as defined in claim 34, wherein the NTG-GMA comprises the magnesium salt of NTG-GMA.

39. A method for sealing pits and fissures in moth enamel as defined in claim 34, wherein the aqueous phosphoric acid has a phosphoric acid concentration in a range from about 10% to about 60% weight to volume.

40. A method for sealing pits and fissures in tooth enamel as defined in claim 34, wherein the aqueous phosphoric acid has a phosphoric acid concentration in a range from about 20% to about 50% weight to volume.

41. A method for sealing pits and fissures in tooth enamel as defined in claim 34, wherein the aqueous phosphoric acid has a phosphoric acid concentration in a range from about 30% to about 45% weight to volume.

42. A method for sealing pits anal fissures in tooth enamel as defined in claim 34, wherein the water miscible organic solvent comprises ethyl alcohol.

43. A method for sealing pits and fissures in tooth enamel as defined in claim 34, wherein the concentration of NTG-GMA within the drying/priming agent is in a range from about 0.4% to about 1.5% by weight of the drying/priming agent.

44. A method for sealing pits anal fissures in tooth enamel as defined in 34, wherein the concentration of NTG-GMA within the drying/priming agent is in a range from about 0.7% to about 1.2% by weight of the drying/priming agent.

45. A method for sealing pits and fissures in tooth enamel as defined in claim 34, wherein the polymerizable resin comprises a resin selected from the group consisting of UDM and Bis-GMA.

46. A method for sealing pits and fissures in tooth enamel as defined in claim 34, wherein the sealing material includes a photopolymerization agent.

47. A method for sealing pits and fissures in tooth enamel as defined in claim 46, wherein the photopolymerization agent comprises TEG-DMA.

48. A method for sealing pits and fissures in tooth enamel as an anticarious procedure comprising the steps of:

(1) etching an area of the surface of the tooth enamel to be treated with an etching solution consisting essentially of an aqueous phosphoric acid solution capable of significantly etching tooth enamel in order to create a more irregular enamel surface to which a polymerizable-resin-containing sealing material can more readily adhere, the aqueous phosphoric acid solution being applied to an area surrounding and including the area of the tooth enamel surface being treated and having a phosphoric acid concentration in a range from about 10% to about 60% weight to volume;

(2) applying a drying/priming agent comprising:
  (a) a water miscible organic solvent (chosen) selected from the group consisting of ethyl alcohol and acetone; and
  (b) NTG-GMA having a concentration in the range from about 0.1% to about 3% by weight of the drying/priming agent, the drying/priming agent being applied to an area surrounding and including the area of the tooth enamel surface being treated; and (3) sealing the enamel surface with a sealing material comprising a polymerizable resin in a concentration sufficient to bond to and substantially seal the area of the tooth enamel surface being treated, the polymerizable resin including Bis-GMA having a concentration in a range from about 20% to about 80% by weight of the sealing material.

49. A method for sealing pits and fissures in tooth enamel as defined in claim 48, wherein the NTG-GMA comprises the sodium salt of NTG-GMA.

50. A method for sealing pits and fissures in tooth enamel as defined in claim 48, wherein the NTG-GMA comprises the magnesium salt of NTG-GMA.

51. A method for sealing pits and fissures in tooth enamel as defined in claim 48, wherein the aqueous phosphoric acid has a phosphoric acid concentration in a range from about 30% to about 50% weight to volume.

52. A method for sealing pits and fissures in tooth enamel as defined in claim 48, wherein the NTG-GMA within the drying/priming agent has a concentration in a range from about 0.4% to about 1.5% by weight of the drying/priming agent.

53. A method for sealing pits and fissures in tooth enamel as defined in claim 48, wherein the water miscible organic solvent comprises ethyl alcohol.

54. A method for sealing pits and fissures in tooth enamel as defined in claim 48, the method including the step of drying the enamel surface with air after step (2) but before step (3).

55. A method for sealing pits and fissures in tooth enamel as defined in claim 48, the method including the step of air aspirating the enamel surface after step (2) but before step (3).

* * * * *

UNITED STATES PATENT AND TRADEMARK OFFICE
CERTIFICATE OF CORRECTION

PATENT NO.   : 5,425,641
DATED        : June 20, 1995
INVENTOR(S)  : DAN E. FISCHER It is certified that error appears in the above-indentified patent and that said Letters Patent is hereby corrected as shown below:

```
     Column 2, line 22, "byproducts" should be --by-products--
     Column 5, line 50, "byproducts" should be --by-products--
     Column 10, line 6, "using a drying/priming agents" should
be --using a drying/priming agent--
     Column 12, lines 5-6, "it took rinse and clean" should be
--it took to rinse and clean--
     Column 12, lines 29-30, "it took rinse and clean" should
be --it took to rinse and clean--
     Column 12, line 38, "tooth-enamel" should be --tooth enamel--
     Column 18, line 59, "to creme" should be --to create--
     Column 19, lines 23-24, "moth enamel" should be --tooth
enamel--
```

Signed and Sealed this

Thirteenth Day of February, 1996

Attest:

BRUCE LEHMAN

*Attesting Officer*    Commissioner of Patents and Trademarks